United States Patent
Nix et al.

(10) Patent No.: US 11,291,428 B2
(45) Date of Patent: Apr. 5, 2022

(54) PROBE COVER

(71) Applicant: Saban Ventures PTY Limited, Alexandria (AU)

(72) Inventors: Sarah Nix, Sydney (AU); Tara Croft, Sydney (AU); Michael Potas, Sydney (AU)

(73) Assignee: Saban Ventures PTY Limited, Alexandria (AU)

( * ) Notice: Subject to any disclaimer, the term of this patent is extended or adjusted under 35 U.S.C. 154(b) by 0 days.

(21) Appl. No.: 17/076,317

(22) Filed: Oct. 21, 2020

(65) Prior Publication Data

US 2021/0113185 A1  Apr. 22, 2021

Related U.S. Application Data

(63) Continuation of application No. 15/772,222, filed as application No. PCT/AU2016/051022 on Oct. 28, 2016, now abandoned.

(30) Foreign Application Priority Data

Oct. 30, 2015 (AU) ................................ 2015904461

(51) Int. Cl.
*A61B 8/00* (2006.01)
*A61B 1/00* (2006.01)
(Continued)

(52) U.S. Cl.
CPC ........ *A61B 8/4422* (2013.01); *A61B 1/00135* (2013.01); *A61B 8/4438* (2013.01);
(Continued)

(58) Field of Classification Search
CPC ............................ A61B 8/4422; A61B 8/4438
(Continued)

(56) References Cited

U.S. PATENT DOCUMENTS 2,947,415 A  8/1960 Garth
3,203,545 A  8/1965 Grossman
(Continued)

FOREIGN PATENT DOCUMENTS

CN  202386706 U  11/2011
DE  202006019618 U1  4/2007
(Continued)

OTHER PUBLICATIONS

International Search Report and Written Opinion issued in PCT/AU2016/051022, dated Dec. 23, 2016, 11 pages.

*Primary Examiner* — Jacob K Ackun
(74) *Attorney, Agent, or Firm* — Stinson LLP

(57) ABSTRACT

A cover for a probe 12, such as an ultrasonic probe, the cover comprising a flexible elongate pouch 1 and a mouth portion 2 for inserting the probe 12 into the pouch, the mouth portion 2 comprising sealing means to enable the mouth portion to be formed into sealing engagement with a proximal end 11 of the probe. Also, a method of preventing a decontaminated ultrasonic probe from contamination comprising the step of, immediately after disinfection, inserting the ultrasonic probe 12 into a cover comprising a flexible elongate pouch 1 and a mouth portion 2 for inserting the probe 12 into to pouch, the mouth portion 2 comprising a deformably rigid portion 3, and deforming the mouth portion 2 into a sealing engagement with a proximal end 11 of the probe, wherein no undisinfected portion of the probe 12 enters the pouch 1.

6 Claims, 4 Drawing Sheets

(51) Int. Cl.
*A61B 46/13* (2016.01)
*A61B 50/30* (2016.01)
*A61B 46/10* (2016.01)
*A61B 46/17* (2016.01)
*A61B 90/00* (2016.01)
*A61B 17/00* (2006.01)

(52) U.S. Cl.
CPC .............. *A61B 46/10* (2016.02); *A61B 46/13* (2016.02); *A61B 46/17* (2016.02); *A61B 50/30* (2016.02); *A61B 2017/00946* (2013.01); *A61B 2090/081* (2016.02)

(58) Field of Classification Search
USPC ........................................................ 206/364
See application file for complete search history.

(56) References Cited

U.S. PATENT DOCUMENTS

| | | | |
|---|---|---|---|
| 3,688,973 | A | 9/1972 | Lillkvist |
| 3,759,438 | A | 9/1973 | Ruda |
| 3,986,648 | A | 10/1976 | Antonini et al. |
| 4,051,994 | A | 10/1977 | Donk et al. |
| 4,159,766 | A | 7/1979 | Kluge |
| 4,561,540 | A | 12/1985 | Hunter et al. |
| 4,754,877 | A | 7/1988 | Johansson et al. |
| 4,815,470 | A | 3/1989 | Curtis et al. |
| 4,878,762 | A | 11/1989 | Uddo, Jr. et al. |
| 4,886,049 | A | 12/1989 | Darras |
| 5,217,001 | A | 6/1993 | Nakao et al. |
| 5,222,600 | A * | 6/1993 | Stoddard .................. A61L 2/26 206/370 |
| 5,228,851 | A | 6/1993 | Burton |
| 5,237,984 | A | 8/1993 | Williams, III et al. |
| 5,325,846 | A | 7/1994 | Szabo |
| 5,337,731 | A * | 8/1994 | Takahashi .............. A61B 50/24 600/109 |
| 5,351,698 | A | 10/1994 | Wheeler et al. |
| 5,355,886 | A * | 10/1994 | Losa Dominguez ........................ A61B 1/00142 600/437 |
| 5,575,747 | A | 11/1996 | Dais et al. |
| 5,667,068 | A | 9/1997 | Weaver |
| 5,715,943 | A | 2/1998 | Thompson, Jr. |
| 5,848,895 | A | 12/1998 | Martin et al. |
| 5,944,179 | A * | 8/1999 | Walker ................... A61B 50/30 206/305 |
| 6,234,310 | B1 * | 5/2001 | Goldhaber .............. B65B 55/02 141/314 |
| 6,267,726 | B1 * | 7/2001 | Grimm .............. A61B 1/00142 600/459 |
| 6,402,695 | B1 | 6/2002 | Grimm |
| 6,594,971 | B1 * | 7/2003 | Addy ................. A61B 1/00144 53/413 |
| 7,665,893 | B2 | 2/2010 | Buchalter |
| 7,879,015 | B2 | 2/2011 | Villefrance et al. |
| 8,110,156 | B2 | 2/2012 | Ricciardi et al. |
| 9,277,966 | B2 | 3/2016 | Seitz, III |
| 10,154,828 | B2 * | 12/2018 | Buchalter ................ B32B 1/08 |
| 2002/0082477 | A1 | 6/2002 | Kim |
| 2005/0143625 | A1 | 6/2005 | Whitmore, III et al. |
| 2006/0264751 | A1 | 11/2006 | Wendelken et al. |
| 2007/0276253 | A1 * | 11/2007 | Park ........................ A61B 8/00 600/461 |
| 2008/0139944 | A1 | 6/2008 | Weymer et al. |
| 2008/0200754 | A1 | 8/2008 | Buchalter |
| 2012/0010468 | A1 * | 1/2012 | Afridi ................ A61B 1/00059 600/121 |
| 2012/0010517 | A1 | 1/2012 | Ma |
| 2012/0269469 | A1 | 10/2012 | Long et al. |
| 2014/0286595 | A1 | 9/2014 | Moreschini |
| 2015/0053582 | A1 | 2/2015 | Lloyd et al. |
| 2015/0090620 | A1 | 4/2015 | Seitz et al. |
| 2015/0320499 | A1 | 11/2015 | Ma |
| 2016/0278738 | A1 * | 9/2016 | Buchalter ................ A61B 8/42 |
| 2016/0303265 | A1 | 10/2016 | Coles |
| 2017/0027658 | A1 | 2/2017 | Black et al. |
| 2017/0296142 | A1 * | 10/2017 | Wodecki .............. A61B 8/4433 |
| 2017/0196646 | A1 | 12/2017 | Ma |
| 2018/0125452 | A1 * | 5/2018 | Sell ...................... A61B 8/4422 |
| 2019/0099233 | A1 * | 4/2019 | Buchalter .............. A61B 46/17 |
| 2019/0167078 | A1 | 6/2019 | Fryer |

FOREIGN PATENT DOCUMENTS

| | | |
|---|---|---|
| WO | 97/11642 A1 | 4/1997 |
| WO | 2007014435 A1 | 2/2007 |
| WO | 2007014436 A1 | 2/2007 |
| WO | 2008024515 A2 | 2/2008 |

* cited by examiner

PROBE COVER

CROSS-REFERENCE TO RELATED APPLICATIONS

This application is a continuation of U.S. patent application Ser. No. 15/772,222, filed Apr. 30, 2018, which is the 371 National Stage Patent Application of International PCT Application No. PCT/AU/2016/051022, filed Oct. 28, 2016 and claims priority of Australian Patent Application No. 2015904461, filed Oct. 30, 2015, the entire contents of which are incorporated herein by reference.

FIELD OF THE INVENTION

The present invention relates to covers for use in protecting disinfected or decontaminated medical instrumentation from recontamination prior to use.

The invention has been developed primarily for use with cabled probes such as intracavity and surface ultrasound probes ("ultrasound probes") or Gamma probes, following disinfection, preferably high level disinfection ("HLD") and is described with reference to such a purpose, however, it will be appreciated that it is not limited solely to that use.

BACKGROUND OF THE INVENTION

Ultrasound probes are used for a variety of intra cavity procedures including intra rectal, intra vaginal and oesophageal examination. Whilst the probes do not need to be completely sterile in most cases, they do need to be subjected to disinfection, usually at least HLD between each use to prevent cross-infection. HLD requires a 6 log reduction in microorganism load.

Ultrasound probes are usually temperature sensitive and cannot be heated above 55-60° C. They can be disinfected by a variety of procedures, such the present Applicant's own aerosol methods, as described in earlier publications WO 2007/014435 and WO 2007/014436.

Typically, after an ultrasound probe has been subjected to HLD, it is stored for some time. The storage environment need not be sterile; however, ideally the probe is maintained in a clean or protected environment to prevent excessive contamination.

The disinfection of ultrasound probes presents special challenges, because the probe is typically constructed integrally with the power and data cable used to link the probe with the console. While the probe itself is always disinfected to some degree, most usually to achieve HLD, the cable projecting from the proximal end of the probe is not. As a precaution, the probe is disinfected to a point well beyond the deepest point of insertion of the probe into the patient. However, there is a point on the cable not far from the probe beyond which no disinfection is applied.

The presence of a potentially contaminated cable attached to a disinfected probe can present problems with storage of the probe between disinfection and patient use.

In some cases, ultrasound probes are stored on racks adjacent to the ultrasound apparatus ready for use. The racks maintain the disinfected, distal end of the probe upwards, with the un-disinfected cable hanging down. While this arrangement provides reasonable separation between the disinfected probe and undisinfected cable, the probe is nevertheless open to the atmosphere and has the potential to become recontaminated from either the environment or handling.

Disinfected probes are sometimes placed into cupboards or drawers. These can provide a relatively clean environment, but there is the possibility in such cases that the undisinfected cable can come into contact with the disinfected portion when being placed into a cupboard or drawer, or space that is otherwise not clean. Further, if an undisinfected probe is accidentally placed in the cupboard or drawer, significant remedial action for the cupboard or drawer and the probes contained therein would be required.

There is a need therefore to store disinfected probes prior to use in such a way that they are protected from the wider environment generally, and the undisinfected cable projecting from their distal end in particular.

It is an object of the present invention to overcome or ameliorate at least one of the disadvantages of the prior art, or to provide a useful alternative.

SUMMARY OF THE INVENTION

According to a first aspect, the invention provides a cover for a probe, the cover comprising a flexible elongate pouch and a mouth portion for inserting the probe into the pouch, the mouth portion comprising sealing means to enable the mouth portion to be formed into sealing engagement with a proximal end of the probe.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The term "seal" means that the cover is engaged with the proximal end of the probe to retain the probe in the cover. The seal may be airtight but that is not necessarily the case.

The probe to be covered may for instance be an ultrasonic probe, such as an intracavity or surface ultrasound probe or other type of diagnostic ultrasound (DU) probe, or it may be a Gamma probe.

Preferably, the pouch is formed from an impermeable plastic material. The pouch may be formed from two opposed elongate sheets of plastic, each sheet having two parallel elongate sides and two parallel short sides, the sheets being fused on each elongate side and on a first short side, the second short side defining a mouth portion.

The sealing means may be a deformably rigid portion. In that case, the mouth portion comprises a deformably rigid strip adjacent and disposed along the second short side. The deformably rigid strip may be a metallic or wire strip. Preferably, it is glued or fused to one elongate sheet.

Alternatively, the sealing means for the mouth portion may and a self adhesive strip, and integrated elastic strip or a Velcro™ strip or similar.

Any suitable means for sealing the pouch around the proximal end of the probe would be suitable.

According to a second aspect, the invention provides a method of preventing a disinfected probe from contamination comprising the step of, immediately after disinfection, inserting the probe into a cover comprising a flexible elongate pouch and a mouth portion for inserting the probe into to pouch, the mouth portion comprising a deformably rigid portion, and deforming the mouth portion into a sealing engagement with a proximal end of the probe, wherein no undisinfected portion of the probe enters the pouch.

The cover is preferably as described above.

Preferably at least a portion of the disinfected probe resides outside the bag when sealed.

In a further aspect, the invention provides a method of the second aspect further comprising the steps of applying to the pouch, when sealed, indicia identifying a unique sterilization cycle, and documenting said indicia against a record of a patent probed with said probe.

The pouch of the present invention is suitable for use for probes that have been disinfected to any level, i.e. low level disinfection, medium level disinfection, and high level disinfection.

BRIEF DESCRIPTION OF THE DRAWINGS

A preferred embodiment(s) of the invention will now be described, by way of example only, with reference to the accompanying drawings(s) in which.

PREFERRED EMBODIMENT OF THE INVENTION

The present invention will now be described with reference to the following examples which should be considered in all respects as illustrative and non-restrictive.

Figure 1:
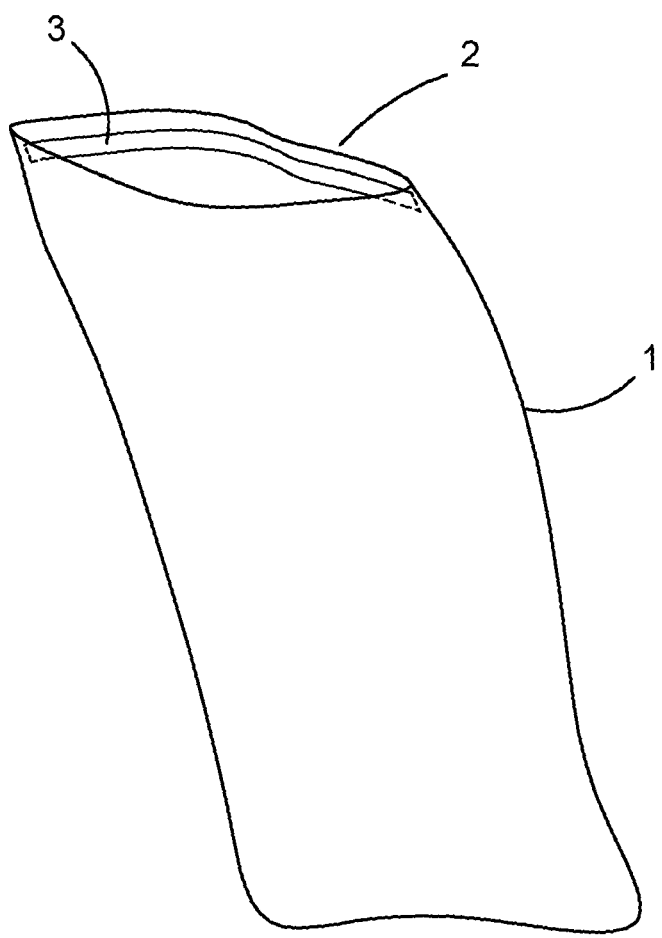
FIG. 1 shows the pouch of the present invention.

As shown in FIG. 1, the cover of the present invention comprises a flexible elongate pouch 1 and a mouth portion 2 for inserting the probe into to pouch.

The pouch portion is, in effect, a plastic bag, sized to hold most intracavity and surface probes, and is impermeable to microorganisms. Any suitable plastic of any gauge can be used provided that it is sufficiently robust to withstand normal use. The pouch is designed to be disposable. In order to accommodate most probes, the pouch is typically 36 cm long and 11 cm wide. The bag may be formed from a single piece of plastic or from two sheets fused around the long sides and side opposite the mouth.

The plastic bag does not need to be sterile, but it does need to be manufactured to high standards, using high grade materials under stringent standards, for instance an ISO certified clean room.

Figure 2:
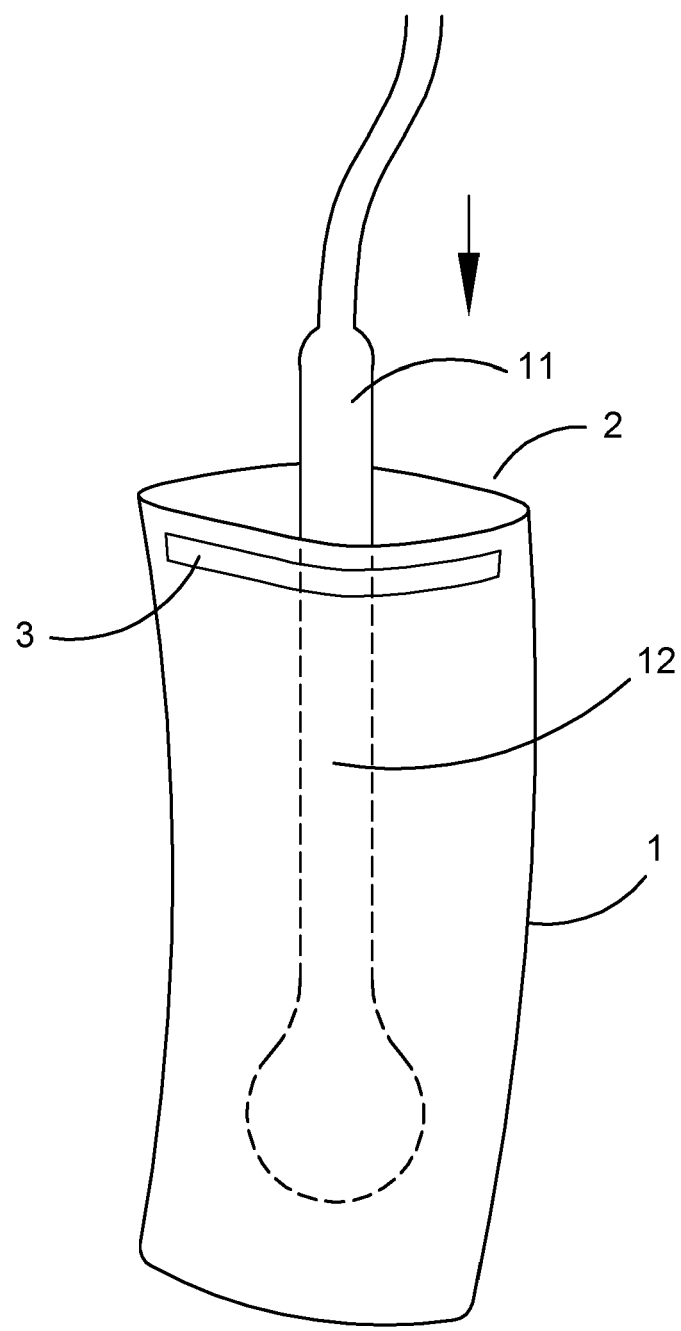
FIG. 2 shows the pouch of the present invention in relation to an ultrasound probe.

As shown in FIG. 2, the mouth portion has a deformably rigid portion 3 to enable the mouth to be closed around the proximal end 11 of the probe 12. This typically is in the form of a metal strip or wire running across the mouth of the pouch. The metal strip or wire may be fused into the plastic or glued to the mouth of the pouch, either on the outside or more preferably inside the pouch.

Figure 3:
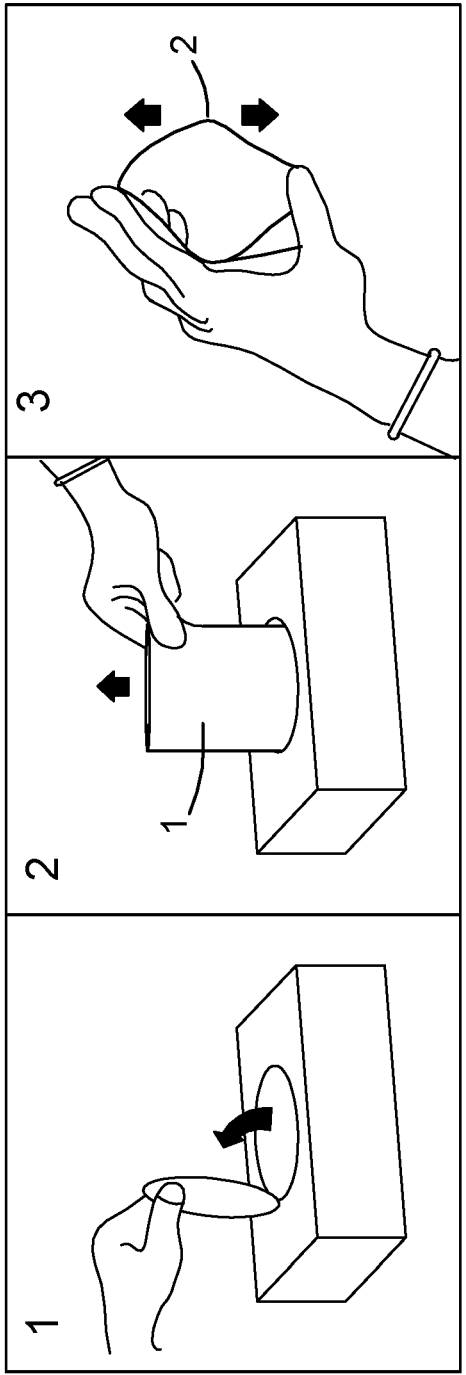
FIG. 3 presents panels 1-6, which show the steps involved in using the pouch of the present invention.
Figure 3:
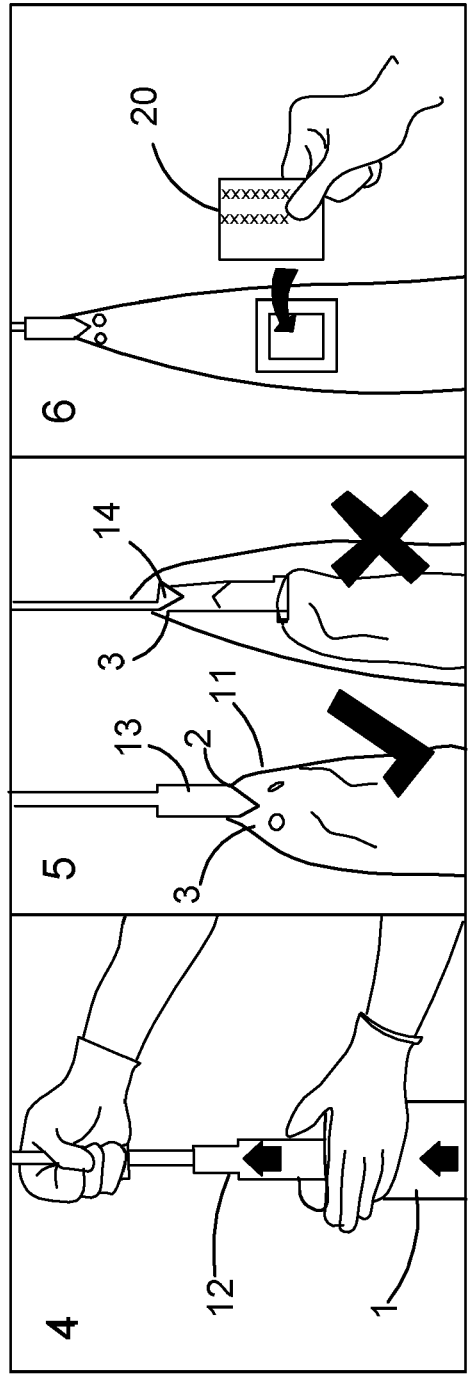

As shown in FIG. 3, particularly panel 4, in use, the probe 12 is inserted into the pouch 1 to approximately the full pouch depth. This takes place as soon as possible after removal of the probe from the decontamination device. When fully inserted, the mouth is then wrapped around the proximal end 11 of the probe, using the deformation of the strip or wire 3 by the user to maintain a sealing arrangement of the bag mouth around the proximal end of the probe. The cable attached to the probe projects from the pouch.

In alternative embodiments, the sealing means is a self adhesive strip. This may be for instance an adhesive strip affixed to the inside of one side of the mouth portion. Preferably, the adhesive strip is covered by a mask which is removed prior to the adhesive portion being used to maintain the sides of the cover in a sealed arrangement around the proximal end of the probe.

In a further alternative embodiment, the sealing means is an integrated elastic strip extending around part or all of the mouth of the pouch. The mouth is expanded as the probe is inserted and allowed to tighten around a proximal end of the probe.

In yet a further embodiment, the sealing means is a Velcro™ strip. The strip can be inside the mouth of the pouch, with a hooked face on one side of the mouth, and an eyelet face on an opposite side. Alternatively, the strip can be on the outside of the pouch, and drawn around the enclosed probe and fastened from the outside.

The sealing means may also be for instance a drawstring running in one or more loops around the mouth of the pouch.

It is important to ensure that the entire portion of the probe within the pouch has been disinfected. A disinfected portion 13 of the probe 12 should project from the mouth of the bag 2, immediately adjacent to it. If an undisinfected portion 14 of the probe is sealed within the pouch 1, the process will be self-defeating.

The probe thus stored in the pouch can be stored in any location without fear of reinfection and particularly without fear of reinfection from the cable.

When it is desired to use the probe, it can be taken to the point of use, unwrapped and immediately put to use. The cover is then discarded. The presence of the cover is an indicator that a probe is clean and it can increase patient confidence.

Figure 4:
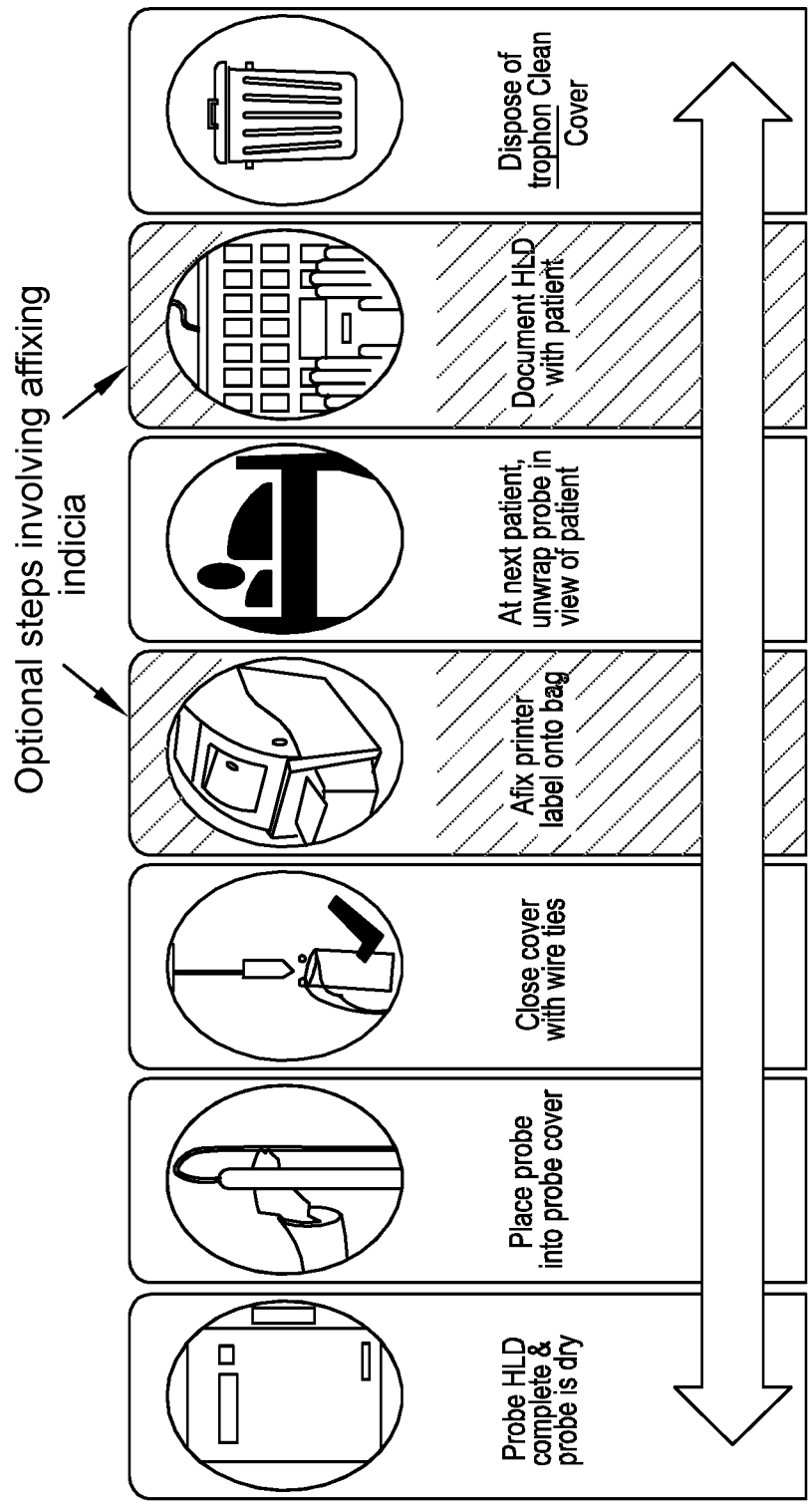
FIG. 4 shows the disinfection process involving the pouch, including optional steps of affixing indicia.

The use of such a bag also has additional advantages in enhancing the traceability of each HLD cycle, as shown in FIG. 4. Traceability means that any defective apparatus or processes can readily be detected.

Once a decontamination cycle has been completed, the article can be placed into the bag as described and the bag and a tag or sticker 20 can be applied bearing the identifying details of the decontamination cycle. In many cases, modern decontamination apparatus can provide a print out of the sterilization details, uniquely identifying the steriliser and the parameters used.

The probe, when ready for use, is then unwrapped. At that stage, the details of the sterilization cycle can be taken from the bag (in physical form, such as peel off sticker, or manually transcribed or digitally acquired) and entered into the patients record.

The cover thus provides a means to link the details of the sterilisation cycle with the individual patient. The present invention allows this to be done much more readily than conventional methodology.

The invention claimed is:

1. A method of preventing a decontaminated ultrasonic probe from contamination comprising:
    as soon as possible after disinfection, inserting the ultrasonic probe into a cover comprising a flexible elongate pouch and a mouth portion for inserting the probe into the pouch, the mouth portion comprising a deformably rigid portion, and
    deforming the deformably rigid portion of the mouth portion to create a seal between the mouth portion and a proximal end of the probe, wherein no undisinfected portion of the probe enters the pouch;
    wherein a disinfected portion of the decontaminated ultrasonic probe resides outside the cover when sealed; and
    wherein the pouch is formed from two opposed elongate sheets of plastic, each sheet having two parallel elongate sides and two parallel short sides, the sheets being fused on each elongate side and on a first short side, the second short side defining the mouth portion.

2. A method according to claim 1 wherein the deformably rigid portion of the mouth portion comprises a deformably rigid strip adjacent and disposed along the second short side.

3. A method according to claim 2 wherein the deformably rigid strip is a metallic or wire strip.

4. A method according to claim 3 wherein the metallic or wire strip is glued or fused to the second short side of one elongate sheet.

5. A method according to claim 1 further comprising the steps of applying to the pouch, when sealed, indicia identifying a unique sterilization cycle, and documenting said indicia against a record of a patient probed with said probe.

6. A method of disinfecting an ultrasonic probe and preventing contamination of the decontaminated ultrasonic probe from contamination comprising:

disinfecting the ultrasonic probe;

as soon as possible after disinfection, inserting the ultrasonic probe into a cover comprising a flexible elongate pouch and a mouth portion for inserting the probe into the pouch, the mouth portion comprising a deformably rigid portion; and deforming the deformably rigid portion of the mouth portion to create a seal between the mouth portion and a proximal end of the probe, wherein no undisinfected portion of the probe enters the pouch;

wherein a disinfected portion of the decontaminated ultrasonic probe resides outside the cover when sealed; and wherein the pouch is formed from two opposed elongate sheets of plastic, each sheet having two parallel elongate sides and two parallel short sides, the sheets being fused on each elongate side and on a first short side, the second short side defining the mouth portion.

\* \* \* \* \*